United States Patent [19]
Haan et al.

[11] Patent Number: 5,645,562
[45] Date of Patent: Jul. 8, 1997

[54] BALLOON CATHETER WITH LIGHT CONDUCTOR

[75] Inventors: Marcel Gerhard Haan, Roden; Hendrikus Cornelis Geert Ligtenberg, Leek, both of Netherlands

[73] Assignee: Cordis Corporation, Miami Lakes, Fla.

[21] Appl. No.: 613,343

[22] Filed: Mar. 11, 1996

[30] Foreign Application Priority Data

Mar. 13, 1995 [NL] Netherlands ............................ 9500495

[51] Int. Cl.$^6$ ................................................. A61M 29/00
[52] U.S. Cl. .......................... 606/194; 606/191; 604/96
[58] Field of Search .................................. 606/191, 194, 606/195; 623/1, 12; 604/96

[56] References Cited

U.S. PATENT DOCUMENTS

| | | |
|---|---|---|
| 4,512,762 | 4/1985 | Spears ..................................... 606/191 |
| 4,773,899 | 9/1988 | Spears . |
| 5,100,429 | 3/1992 | Sinofsky et al. . |
| 5,125,925 | 6/1992 | Lundahl . |

FOREIGN PATENT DOCUMENTS

| | | |
|---|---|---|
| 0646360A1 | 5/1993 | European Pat. Off. . |
| 0646360A1 | 5/1994 | European Pat. Off. . |

*Primary Examiner*—Michael Buiz
*Assistant Examiner*—Kevin Truong
*Attorney, Agent, or Firm*—Gerstman, Ellis & McMillin, Ltd.

[57] ABSTRACT

A balloon catheter comprising a tube-like basic body with a distal end and a proximal end and a balloon member positioned adjacent the distal end. A first light conductor extends from the proximal end into the balloon member, with the first light conductor having a light-absorbing section adjacent the proximal end and a light-emitting section at a location within the balloon. A second light conductor is connected to and continuous with the first light conductor and forms a continuous light conductor tracing a loop inside the balloon member. The second light conductor is operative to sense light emitted by the light-emitting section of the first light conductor. The second light conductor also has a light-emitting section at a location adjacent the proximal end.

10 Claims, 1 Drawing Sheet

BALLOON CATHETER WITH LIGHT CONDUCTOR

FIELD OF THE INVENTION

The present invention concerns a novel balloon catheter and, more particularly, a balloon catheter having a source of light within the balloon.

BACKGROUND OF THE INVENTION

Balloon catheters with light sources are known in the prior art. For example, see Lundahl U.S. Pat. No. 5,125,925; Sinofsky et al. U.S. Pat. No. 5,100,429; Spears U.S. Pat. No. 4,773,899; and European Patent Application EPO 646 360.

We have discovered a novel balloon catheter which is simple in construction and efficient to manufacture, and which enables information to be obtained with respect to the quantity of light emitted, so that the light can be controlled by an operator. Utilizing the balloon catheter of the present invention in which a light-emitting source is present, it is possible, for instance, to fit a stent into the vascular system of a patient, which stent is made of a plastic material that cures under the action of light. In particular, such a stent could cure under the action of a controlled amount of UV light inside the body of a patient following expansion. The balloon member can be utilized to effect the expansion of the stent and as a result of the controlled amount of light emitted within the balloon, the material of which the stent has been made cures, so that it retains its expanded form.

Therefore, it is an object of the present invention to provide a balloon catheter having a light source within the balloon, for use in the vascular system of a patient.

Another object of the present invention is to provide a balloon catheter in which the intensity and quantity of the light emitted can be controlled.

A still further object of the present invention is to provide a balloon catheter having an internal light source which is simple in construction and efficient to manufacture.

Other objects and advantages of the invention will become apparent as the description proceeds.

SUMMARY OF THE INVENTION

In accordance with the present invention, a balloon catheter is provided which includes a tube-like basic body with a distal end and a proximal end. A balloon member is positioned adjacent the distal end. A first light conductor extends from the proximal end into the balloon. The first light conductor has a light-absorbing section adjacent the proximal end and a light-emitting section at a location within the balloon. A second light conductor is connected to and is contiguous with the first light conductor. The second light conductor has a light-emitting section at a location adjacent the proximal end. The second light conductor is operative to sense light emitted by the light-emitting section of the first light conductor.

In one embodiment, the second light conductor has a light-absorbing section located within the balloon for sensing light emitted by the first light conductor.

In illustrative embodiments, the first light conductor and the second light conductor form a continuous light conductor tracing a loop inside the balloon. The light-emitting section of the first light conductor is constructed to emit light in a radial direction and the first light conductor comprises an optic fiber bundle with the light-emitting section comprising a roughened portion of the optic fiber bundle. In the illustrative embodiment, the second light conductor also comprises an optic fiber bundle.

Utilizing the present invention, during the treatment of the patient, information can be obtained by means of the light sensor with respect to the intensity of the quantity of light actually emitted by the light-emitting end of the first light conductor, so that the intensity and quantity of the light emitted can be controlled. Consequently, it is possible to accurately control the supply of light. When used in the implantation of a stent in which the balloon member effects the expansion of the stent and the emitted light cures the stent material, the control of the supply of light may aid in controlling the curing of the stent.

In the illustrative embodiment, the light conductors can have a small diameter, so that the overall diameter of the basic body of the catheter can remain relatively small. By having the second light conductor connected to and continuous with the first light conductor, the sensor of the second light conductor can measure the intensity of the quantity of residual light emerging from the end face of the first light conductor, so that it is possible to accurately determine the quantity of light actually emitted. This equals the light energy supplied minus the light energy removed by the sensor.

In accordance with the illustrative embodiment, by forming a continuous light conductor which traces a loop inside the balloon member, the accuracy of the measurement will be enhanced because measuring errors resulting from unknown emission of light at a transition between the two conductors will not occur. By emitting light in a radial direction, the element to be exposed to the light, for example the stent, will be exposed evenly so that the curing may take place uniformly.

A more detailed explanation of the invention is provided in the following description and claims, and is illustrated in the accompanying drawings.

DETAIL DESCRIPTION OF THE ILLUSTRATIVE EMBODIMENT

Figure 1:
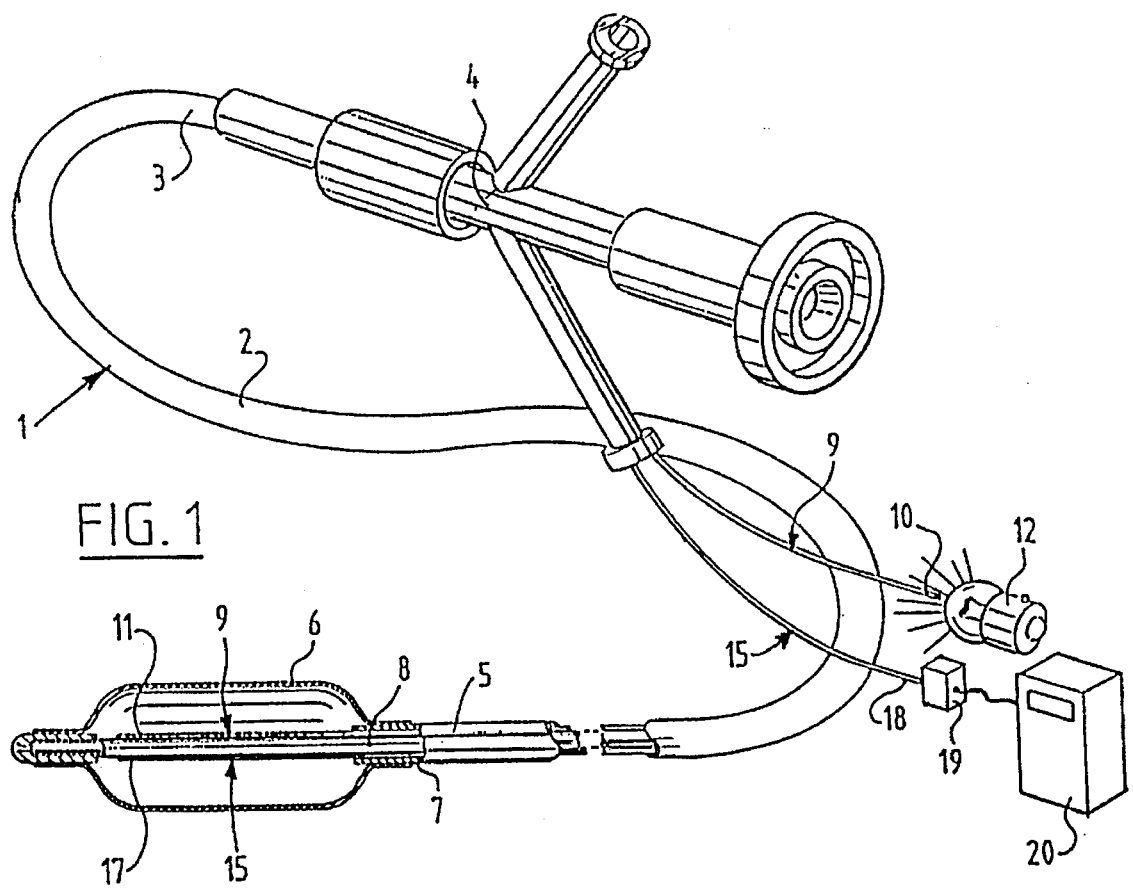
FIG. 1 is a schematic illustration of a catheter constructed in accordance with the principles of the present invention, with the distal end section being illustrated in partial cross-section and at an enlarged scale.

The catheter 1 according to the invention as illustrated in FIG. 1 comprises in the usual manner a tube-like basic body 2 with a proximal end 3 and a distal end 5. The proximal end 3, which remains outside the body of a patient during treatment, is provided with a connecting member 4 for one or more lumens inside the basic body 2.

At the distal end 5, the basic body 2 supports a balloon member 6. As can be seen in FIG. 1, the basic body 2 is made up of an outer tube-like member 7, inside a lumen whereof an inner tube-like member 8 has been received. The balloon member 6 has been arranged with its relatively proximal end to the end of the outer tube-like member 7 and is, with its relatively distal end, connected adjacent to the distal end of the inner tube-like member 8. Via the channel remaining inside the lumen of the outer tube-like member 7, a liquid or gas under pressure can be supplied from the connecting member 4 to the balloon 6, in order to expand the balloon 6. The inner tube-like member 8 also comprises a lumen, which can serve as guiding channel for a guide wire.

Catheter 1 also comprises a first light conductor 9 which extends from the proximal end of the catheter to the distal end 5 thereof. At the proximal end 3 the light conductor 9 is led outside through the connecting member 4. The proximal end of the light conductor 9 forms a light-absorbing end-section 10, which has been made in such a way that it can conduct light, emitted by a source of light 12 (illustrated schematically), to the light conductor 9.

At the opposite, distal end-section, the light conductor 9 comprises a light-emitting end 11, which is situated inside the balloon member 6. This light-emitting end 11 has been treated in such a manner, in particular, roughened by grinding, that the light conducted through the conductor is emitted from the light-emitting end-section 11 in a radial direction.

Catheter 1 is also provided with a light sensor, with which the quantity of light emitted by the light-emitting end-section 11, and in particular the intensity thereof, can be determined. This sensor comprises a second light conductor 15, comprising a light-absorbing end 17, also situated inside the balloon member 6, and at the opposite, proximal end a light-emitting end-section 18. In this embodiment a light-sensitive cell 19 is connected to the light-emitting end-section 18. This light-sensitive cell 19 is in turn connected to a processing device 20, which processes the signal coming from the light-sensitive cell 19.

Thus the second light conductor 15 forms a light sensor of which the light-absorbing end 17 is a light-sensitive element; the section of the conductor extending through the basic body 2 to the proximal end forms a conductor conducting a light-dependent signal to this proximal end.

With another embodiment (not shown), the light sensor can also comprise a light-sensitive cell inside the balloon member 6, which conducts the light-dependent signal via electrical conductors to the proximal end, for further processing.

The processing device 20 gives an indication of, in particular, the intensity of the light inside the balloon member 6. Depending on the value measured, the light source 12 can be controlled in order to obtain the appropriate intensity required, such as for the purpose of curing the plastic material of a stent that is being implanted. The processing device 20 can be connected directly to the light source 12, so that a feedback control system for the light intensity is obtained.

With the embodiment shown in FIG. 1, the light-absorbing end 17 of the second light conductor 15 absorbs light along at least a significant section of the end extending inside the balloon member 6. The value measured consequently depends on the actual light intensity inside the balloon member.

It is, however, also possible to detect the quantity of light that has not been emitted by light conductor 9 into the balloon, in order to deduce from that and from the light intensity supplied, how much light has actually been emitted.

Figure 2:
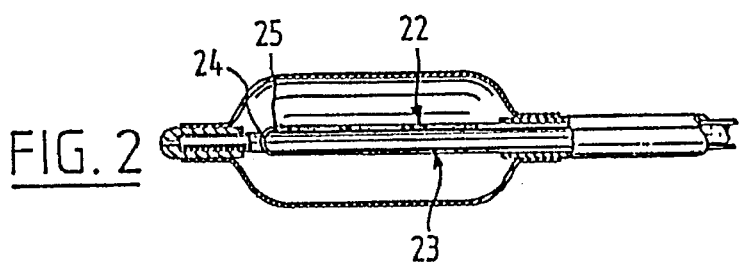
FIG. 2 is a view of the distal end section corresponding to FIG. 1 but of an alternative embodiment.
Figure 3:
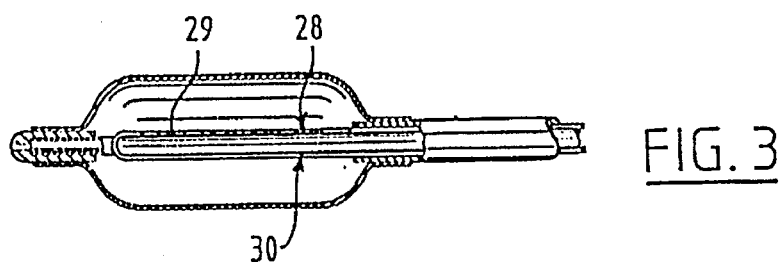
FIGS. 3 is a view of a distal end section corresponding to FIG. 1 of yet another embodiment.

This has been employed with the embodiments illustrated in the FIGS. 2 and 3.

In FIG. 2, the light conductor comprising the light-emitting end-section has been indicated with the number 22, and the second light conductor comprising the light-absorbing end-section with the number 23. The end-face of the second light conductor 23 is connected to the end-surface 25 of the first light conductor 22. The second light conductor 23 has been positioned, as illustrated, in a loop 24, in order to obtain a feedback connection of which the constituent parts are positioned in line with each other.

With this embodiment it can be seen that the light sensor determines the quantity of residual light at the end surface of the first light conductor 22 supplying the light. Thus it can be determined how much light has been emitted by the light-emitting end of the light conductor 22.

As far as the principle involved is concerned, FIG. 3 shows an embodiment corresponding to the embodiment of FIG. 2. However, in this case the light conductors form one continuous light conductor 29 tracing a loop inside the balloon member. The first light conductor 28 forms the supplying light conductor and the section 30, extending in a parallel fashion, forms the second, feedback light-removing light conductor.

The light-emitting end-sections of the first light conductor have been treated in such a way that the light conveyed by the light conductor is emitted radially in this light-emitting end-section. This can be achieved for instance by roughening the surface of the light conductor, for instance by grinding.

It can be seen that a novel balloon catheter has been provided in which there is a first light conductor having a light source within the balloon member and a second light conductor connected with and continuous with the first light conductor within the balloon member. By utilizing the principles of the present invention, the supply of light can be controlled accurately.

Although illustrative embodiments of the invention have been shown and described, it is to be understood that various modifications and substitutions may be made by those skilled in the art without departing from the novel spirit and scope of the present invention.

We claim:

1. A balloon catheter, which comprises:
   a tube-like basic body with a distal end and a proximal end;
   a balloon member positioned adjacent said distal end;
   a first light conductor extending from said proximal end into said balloon member;
   said first light conductor having a light-absorbing section adjacent said proximal end and a light-emitting section at a location within said balloon member;
   a second light conductor connected to and continuous with said first light conductor;
   said second light conductor having a light-emitting section at a location adjacent said proximal end to provide feedback of light emitted from the light-emitting section of said first light conductor.

2. A balloon catheter as defined by claim 1, said second light conductor having a light-absorbing section within said balloon member, said light-absorbing section of said second light conductor being operative to sense light emitted by said light-emitting section of said first light conductor.

3. A balloon catheter as defined in claim 1, said first light conductor and said second light conductor forming a continuous light conductor tracing a loop inside said balloon member.

4. A balloon catheter as defined by claim 1, said light emitting section of said first light conductor constructed to emit light in a radial direction.

5. A balloon catheter as defined by claim 1, said first light conductor comprising an optic fiber bundle with said lightemitting section comprising a roughened portion of said optic fiber bundle.

6. A balloon catheter as defined by claim 5, said second light conductor comprising an optic fiber bundle.

7. A balloon catheter, which comprises:

a tube-like basic body with a distal end and a proximal end;

a balloon member positioned adjacent said distal end;

a first light conductor extending from said proximal end into said balloon member;

said first light conductor having a light-absorbing section adjacent said proximal end and a light-emitting section at a location within said balloon member;

a second light conductor connected to and continuous with said first light conductor, said first light conductor and said second light conductor forming a continuous light conductor tracing a loop inside said balloon;

said second light conductor being operative to sense light emitted by said light-emitting section of said first light conductor;

said second light conductor having a light-emitting section at a location adjacent said proximal end to provide feedback of light emitted from the lightemitting section of said first light conductor.

8. A balloon catheter as defined by claim 7, said light-emitting section of said first light conductor constructed to emit light in a radial direction.

9. A balloon catheter as defined by claim 7, said first light conductor comprising an optic fiber bundle with said light-emitting section comprising a roughened portion of said optic fiber bundle.

10. A balloon catheter as defined by claim 9, said second light conductor comprising an optic fiber bundle.

* * * * *